(12) United States Patent
Nagatomo et al.

(10) Patent No.: US 8,222,446 B2
(45) Date of Patent: Jul. 17, 2012

(54) METHOD FOR PRODUCING DIHYDROXYBENZENE DERIVATIVE

(75) Inventors: Akinori Nagatomo, Omuta (JP); Kouki Oogaki, Otake (JP); Takeshi Kobayashi, Omuta (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 155 days.

(21) Appl. No.: 12/918,852

(22) PCT Filed: Mar. 19, 2008

(86) PCT No.: PCT/JP2008/055144
§ 371 (c)(1),
(2), (4) Date: Aug. 23, 2010

(87) PCT Pub. No.: WO2009/116156
PCT Pub. Date: Sep. 24, 2009

(65) Prior Publication Data
US 2011/0004013 A1    Jan. 6, 2011

(51) Int. Cl.
*C07C 69/675* (2006.01)
(52) U.S. Cl. ......................................... 560/75
(58) Field of Classification Search .................. None
See application file for complete search history.

(56) References Cited

U.S. PATENT DOCUMENTS

| | | | |
|---|---|---|---|
| 5,266,661 A | 11/1993 | Earls et al. | |
| 2006/0205971 A1 | 9/2006 | Tsukamoto et al. | |

FOREIGN PATENT DOCUMENTS

| | | |
|---|---|---|
| JP | 56-14526 A | 2/1981 |
| JP | 2-232220 A | 9/1990 |
| JP | 7-118621 A | 5/1995 |
| JP | 2001-234140 A | 8/2001 |
| JP | 2008-127285 A | 6/2008 |
| JP | 2008-127286 A | 6/2008 |
| WO | 2005/087704 | 9/2005 |

OTHER PUBLICATIONS

International Search Report (PCT/ISA/210) issued on Jun. 24, 2008, by Japanese Patent Office as the International Searching Authority for International Application No. PCT/JP2008/055144.

*Primary Examiner* — Kamal Saeed
(74) *Attorney, Agent, or Firm* — Buchanan Ingersoll & Rooney PC

(57) ABSTRACT

A method of producing a compound represented by the following general formula (3):

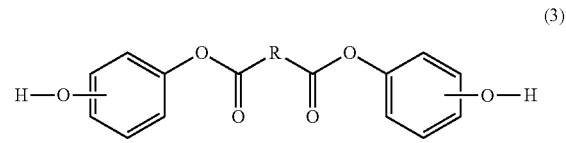

(3)

[wherein R is a bivalent aliphatic group having a carbon number of 1-16 or a bivalent aromatic group], which comprises a step (i) of reacting a compound represented by the following general formula (1):

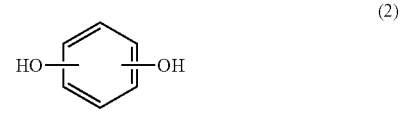

(2)

with a carboxylic acid halide represented by the following general formula (2):

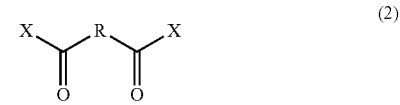

(2)

[wherein R is a bivalent aliphatic group having a carbon number of 1-16 or a bivalent aromatic group and X is a halogen atom] in the presence of a basic compound to form an ester, and a step (ii) of conducting a heat treatment after the step (i) to decompose an oligomer in the ester.

10 Claims, No Drawings

METHOD FOR PRODUCING DIHYDROXYBENZENE DERIVATIVE

TECHNICAL FIELD

This invention relates to a method for producing a dihydroxybenzene derivative, and more particularly to a method for producing a dihydroxybenzene derivative such as resorcin diester-based compound or the like used for the purpose of improving an adhesion durability between a metal reinforcement such as steel cord or the like and rubber, which are used in rubber articles such as pneumatic tires, industrial belts and so on.

RELATED ART

In rubber articles particularly requiring strength such as tires for automobiles, conveyor belts, hoses and the like, there are used composite materials formed by covering metal reinforcements such as steel cords or the like with a rubber composition for the purpose of reinforcing rubber to improve strength and durability. In order that the rubber-metal composite material develops a high reinforcing effect and provides reliability, stable adhesion is required between rubber and the metal reinforcement independently of conditions of mixing, compounding, storing and the like. In order to obtain such a composite material, there is widely used a so-called direct vulcanization adhesion that metal reinforcements such as steel cords or the like plated with zinc, brass or the like are embedded in a rubber composition compounded with sulfur and adhered thereto at a time of curing rubber during the vulcanization under heating. Until now, there are made various examinations for improving the adhesiveness between rubber and metal reinforcement through the direct vulcanization adhesion, particularly resistant adhesiveness to moist heat.

For instance, there is reported a rubber composition compounded with a resorcin-formaldehyde resin (hereinafter abbreviated as "RF resin") obtained by condensation of resorcin or resorcin and formalin for the purpose of improving the resistant adhesiveness to moist heat (JP-A-2001-234140). Also, there is reported an adhesive material comprised of a mixed polyester with a resorcin skeleton having an weight average molecular weight of 3000-45000 (JP-A-H07-118621).

On the other hand, the inventors have reported a dihydroxybenzene derivative capable of further improving the resistant adhesiveness to moist heat such as resorcin diester compounds and the like as well as a composition thereof (WO 2005-087704).

However, the dihydroxybenzene derivative is typically produced by reacting dihydroxybenzene with a bivalent carboxylic acid halide in the presence of a basic compound, but the reproducibility on yield (crude) and composition (ratio of diester body/oligoester body) is not obtained. That is, the properties of the resulting cake differ in accordance with the ratio of diester body/oligoester body and there is a problem on the scattering of the yield (crude). Especially, when the oligoester body is rich, the cake is violently gooey and may not be obtained as a solid. Also, the difference of the composition (ratio of diester body/oligoester body) does not largely exert on the resistant adhesiveness to moist heat, but results in differences on basic properties such as handling, melting point and so on, so that there is caused a problem in the quality control.

It is, therefore, the first object of the invention to provide a method for producing a dihydroxybenzene derivative by reacting dihydroxybenzene with a bivalent carboxylic acid halide wherein a composition (ratio of diester body/oligoester body) can be reproduced stably to maintain a higher yield (crude).

Also, it is usually required to produce the dihydroxybenzene derivative by reacting an excessive amount of dihydroxybenzene with the bivalent carboxylic acid halide in the presence of a basic compound. In practice, the process must be optimized by efficiently recovering dihydroxybenzene as a starting material.

It is the second object of the invention to provide an optimized method for producing a dihydroxybenzene derivative by reacting dihydroxybenzene with a bivalent carboxylic acid halide wherein it is possible to recover dihydroxybenzene efficiently.

The inventors have made various studies for ensuring the reproducibility and found that when dihydroxybenzene and the bivalent carboxylic acid halide are only reacted at a relatively low temperature, the composition is rich in the oligoester body, and subsequently the oligoester body is reacted with the remaining dihydroxybenzene to change into the diester body by heat history in the isolation course. Also, it has been confirmed that the bivalent carboxylic acid halide is poor in the heat stability and is not durable in the reaction at a higher temperature. So, it has been found out that the reproducibility on the composition and yield (crude) is obtained by such a two-stage reaction that dihydroxybenzene and the bivalent carboxylic acid halide are reacted at a relatively low temperature to completely convert skeleton of carboxylic acid halide into a diester body or an oligoester body and thereafter the oligoester body is changed into a diester body by ester interchange reaction with an excessive amount of dihydroxybenzene at a higher temperature.

Also, the inventors have made further studies and found that dihydroxybenzene derivatives can be produced efficiently through simple operation by optimizing a combination of unit operations such as reaction, isolation, dihydroxybenzene recover and so on, and as a result, the invention has been accomplished.

That is, the production method of the invention is characterized by comprising a step (i) of reacting a compound represented by the following general formula (1):

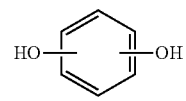

with a carboxylic acid halide represented by the following general formula (2):

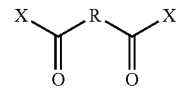

[wherein R is a bivalent aliphatic group having a carbon number of 1-16 or a bivalent aromatic group and X is a halogen atom] in the presence of a basic compound to form an ester, and a step (ii) of conducting a heat treatment after the step (i) to decompose an oligomer in the ester, and can produce a compound represented by the following general formula (3):

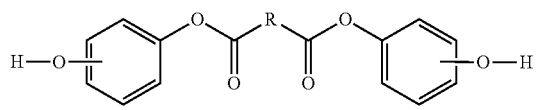

(3)

[wherein R is a bivalent aliphatic group having a carbon number of 1-16 or a bivalent aromatic group].

In a preferable embodiment of the production method of the invention, the compound of the general formula (1) is reacted at a molar ratio of 4-30 times with the carboxylic acid halide of the general formula (2).

In another preferable embodiment of the production method of the invention, the step (i) of forming the ester is carried out at −20° C. to 80° C.

In the other preferable embodiment of the production method of the invention, the step (ii) of decomposing the oligomer is carried out at 110° C. to 140° C.

In the production method of the invention, the basic compound is preferable to be an organic base.

In the production method of the invention, the compound of the general formula (3) is preferable to a compound represented by the following general formula (4):

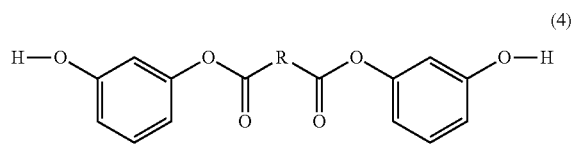

(4)

[wherein R is a bivalent aliphatic group having a carbon number of 1-16 or a bivalent aromatic group].

Also, a preferable embodiment of the production method of the invention includes a step (a) of dissolving or suspending the compound of the general formula (1) in an organic solvent substantially immiscible with water and partially neutralizing with the basic compound;

a step (b) of adding the carboxylic acid halide of the general formula (2) dropwise and reacting to form an ester;

a step (c) of conducting a heat treatment at a temperature higher than that of the step (b) to decompose an oligomer in the ester;

a step (d) of contacting a mixture obtained in the step (c) with water to precipitate a product and subjecting to a solid-liquid separation operation and a drying to obtain a solid of the product;

a step (e) of adding an organic solvent substantially immiscible with water to a discharged water produced by the solid-liquid separation operation of the step (d) to extract an unreacted compound of the general formula (1) used as a starting material; and a step (f) of adjusting a concentration in a solution of the compound of the general formula (1) in the organic solvent substantially immiscible with water obtained at the step (e) so as to render into a starting material in the step (a). At this moment, the organic solvent substantially immiscible with water is preferable to be selected from organic solvents of ketone series, ether series and ester series. In the step (e), it is preferable that pH of water layer in the extraction of the unreacted compound of the general formula (1) used as a starting material is adjusted to 6.5-7.5.

In the production method of the invention, the compound of the general formula (4) may contain 0-30 weight % of a compound represented by the following general formula (5):

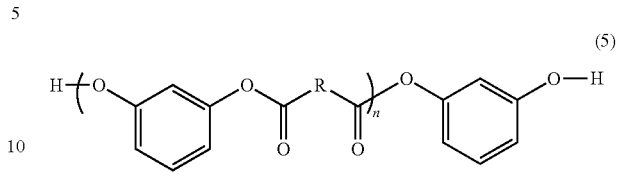

(5)

[wherein R is a bivalent aliphatic group having a carbon number of 1-16 or a bivalent aromatic group and n is an integer of 2-6].

According to the invention, there can be provided the method for reproducibly producing dihydroxybenzene derivatives used for the purpose of improving the adhesion durability between rubber and metal reinforcement such as steel cords or the like used in rubber articles such as pneumatic tires, industrial belts and so on. Also, according to the invention, there can be provided the method for producing dihydroxybenzene derivatives efficiently in a simple operation.

BEST MODE FOR CARRYING OUT THE INVENTION

The invention will be described in detail below. The production method of the compound represented by the general formula (3) according to the invention is characterized by comprising a step (i) of reacting the compound of the general formula (1) with the carboxylic acid halide of the general formula (2) in the presence of the basic compound to produce an ester and a step (ii) of conducting a heat treatment after the step (i) to decompose an oligomer in the ester.

As the compound of the general formula (1) are mentioned catechol, resorcin and hydroquinone. Among them, resorcin is preferable.

In the carboxylic acid halide of the general formula (2), R is a bivalent aliphatic group having a carbon number of 1-16 or a bivalent aromatic group. As the bivalent aliphatic group having a carbon number of 1-16 are mentioned, for example, a straight-chain or branched-chain alkylene group such as methylene group, ethylene group, butylene group, isobutylene group, octylene group, 2-ethylhexylene group or the like; a straight-chain or branched chain alkenylene group such as vinylene group (ethenylene group), butenylene group, octenylene group or the like; an alkylene or alkenylene group in which hydrogen atom of the alkylene group or alkenylene group is substituted with hydroxyl group, amino group or the like; and an alicyclic group such as cyclohexylene group or the like. As the bivalent aromatic group are mentioned a substitutable phenylene group, substitutable naphthylene group, biphenyl group, diphenylether group and so on. Among them, an alkylene group having a carbon number of 2-10 or phenylene group are desirable, and ethylene group, butylene group and octylene group are particularly preferable considering easy availability and the like.

In the carboxylic acid halide of the general formula (2), X is a halogen atom. As the halogen atom are preferable chlorine and bromine.

As the carboxylic acid halide of the general formula (2) are mentioned an aliphatic dicarboxylic acid dichloride such as malonic acid dichloride, succinic acid dichloride, fumaric acid dichloride, maleic acid dichloride, glutaric acid dichloride, adipic acid dichloride, suberic acid dichloride, azelaic acid dichloride, sebacic acid dichloride, 1,10-decanedicarboxylic acid dichloride, 1,12-dodecanedicarboxylic acid dichloride, 1,16-hexadecanedicarboxylic acid dichloride or the like; an alicyclic dicarboxylic acid dichloride such as cyclohexanedicarboxylic acid dichloride, cyclohexenedicarboxylic acid dichloride or the like; an aromatic dicarboxylic acid dichloride such as isophthalic acid dichloride, terephthalic acid dichloride or the like; an aliphatic dicarboxylic acid dibromide such as malonic acid dibromide, succinic acid dibromide, fumaric acid dibromide, maleic acid dibromide, glutaric acid dibromide, adipic acid dibromide, suberic acid dibromide, azelaic acid dibromide, sebacic acid dibromide, 1,10-decanedicarboxylic acid dibromide, 1,12-dodecanedicarboxylic acid dibromide, 1,16-hexadecanedicarboxylic acid dibromide or the like; an alicyclic dicarboxylic acid dibromide such as cyclohexanedicarboxylic acid dibromide, cyclohexenedicarboxylic acid dibromide or the like; and an aromatic dicarboxylic acid dibromide such as isophthalic acid dibromide, terephthalic acid dibromide or the like. Among them, malonic acid dichloride, succinic acid dichloride, adipic acid dichloride, azelaic acid dichloride, sebacic acid dichloride, terephthalic acid dichloride, isophthalic acid dichloride, malonic acid dibromide, succinic acid dibromide, adipic acid dibromide, azelaic acid dibromide, sebacic acid dibromide, terephthalic acid dibromide and isophthalic acid dibromide are preferable.

As the compound of the general formula (3) are mentioned, for example, compounds of the general formula (4). Moreover, R in the general formulae (3) and (4) is the same meaning as R in the general formula (2).

As a concrete example of the compound represented by the general formula (3) are mentioned malonic acid bis(2-hydroxyphenyl) ester, succinic acid bis(2-hydroxyphenyl) ester, fumaric acid bis(2-hydroxyphenyl) ester, maleic acid bis(2-hydroxyphenyl) ester, malic acid bis(2-hydroxyphenyl) ester, itaconic acid bis(2-hydroxyphenyl) ester, citraconic acid bis(2-hydroxyphenyl) ester, adipic acid bis(2-hydroxyphenyl) ester, tartaric acid bis(2-hydroxyphenyl) ester, azelaic acid bis(2-hydroxyphenyl) ester, sebacic acid bis(2-hydroxyphenyl) ester, cyclohexanedicarboxylic acid bis(2-hydroxyphenyl) ester, terephthalic acid bis(2-hydroxyphenyl) ester, isophthalic acid bis(2-hydroxyphenyl) ester, malonic acid bis(3-hydroxyphenyl) ester, succinic acid bis(3-hydroxyphenyl) ester, fumaric acid bis(3-hydroxyphenyl) ester, maleic acid bis(3-hydroxyphenyl) ester, malic acid bis(3-hydroxyphenyl) ester, itaconic acid bis(3-hydroxyphenyl) ester, citraconic acid bis(3-hydroxyphenyl) ester, adipic acid bis(3-hydroxyphenyl) ester, tartaric acid bis(3-hydroxyphenyl) ester, azelaic acid bis(3-hydroxyphenyl) ester, sebacic acid bis(3-hydroxyphenyl) ester, cyclohexanedicarboxylic acid bis(3-hydroxyphenyl) ester, terephthalic acid bis(3-hydroxyphenyl) ester, isophthalic acid bis(3-hydroxyphenyl) ester, malonic acid bis(4-hydroxyphenyl) ester, succinic acid bis(4-hydroxyphenyl) ester, fumaric acid bis(4-hydroxyphenyl) ester, maleic acid bis(4-hydroxyphenyl) ester, itaconic acid bis(4-hydroxyphenyl) ester, citraconic acid bis(4-hydroxyphenyl) ester, adipic acid bis(4-hydroxyphenyl) ester, tartaric acid bis(4-hydroxyphenyl) ester, azelaic acid bis(4-hydroxyphenyl) ester, sebacic acid bis(4-hydroxyphenyl) ester, cyclohexanedicarboxylic acid bis(4-hydroxyphenyl) ester, terephthalic acid bis(4-hydroxyphenyl) ester, isophthalic acid bis(4-hydroxyphenyl) ester and so on.

Among them, malonic acid bis(3-hydroxyphenyl) ester, succinic acid bis(3-hydroxyphenyl) ester, fumaric acid bis(3-hydroxyphenyl) ester, maleic acid bis(3-hydroxyphenyl) ester, malic acid bis(3-hydroxyphenyl) ester, itaconic acid bis(3-hydroxyphenyl) ester, citraconic acid bis(3-hydroxyphenyl) ester, adipic acid bis(3-hydroxyphenyl) ester, tartaric acid bis(3-hydroxyphenyl) ester, azelaic acid bis(3-hydroxyphenyl) ester, sebacic acid bis(3-hydroxyphenyl) ester and cyclohexanedicarboxylic acid bis(3-hydroxyphenyl) ester are preferable, and particularly succinic acid bis(3-hydroxyphenyl) ester, adipic acid bis(3-hydroxyphenyl) ester and sebacic acid bis(3-hydroxyphenyl) ester are preferable.

In the step (i) of the production method of the invention or "esterification step", the compound of the general formula (1) and the dicarboxylic acid halide of the general formula (2) are reacted in the presence of the basic compound. At this stage, a significant amount of an oligoester body represented by the general formula (5) is existent in the reaction product in addition to the objective compound of the general formula (3), particularly the compound of the general formula (4). In the step (ii) or "oligomer decomposition step", therefore, heat treatment is conducted to convert the oligoester body of the general formula (5) into the compound of the general formula (3), particularly the compound of the general formula (4) through ester exchange reaction with the compound (e.g. resorcin) of the general formula (1) excessively remaining after the esterification step.

The basic compound used in the esterification step (i) may be an organic base or an inorganic base. As the organic base are mentioned pyridine, β-picoline, N-methylmorpholine, dimethylaniline, diethylaniline, and organic amines such as trimethylamine, triethylamine, tributylamine and the like. As the inorganic base are mentioned an alkali metal hydroxide such as sodium hydroxide, potassium hydroxide or the like; and an alkali metal carbonate such as potassium carbonate, sodium carbonate or the like. Among them, the organic bases having also an action as a solvent are preferable, and particularly pyridine, β-picoline, N-methylmorpholine, dimethylaniline and the like are preferable considering the basicity and the like.

The amount of the basic compound used in the esterification step (i) is not particularly limited and may be enough to ensure a fluidity capable of dissolving the compound of the general formula (1) with stirring at the reaction temperature of the esterification step (i). Usually, it is used in an amount of ½ to 3 times by weight of the compound of the general formula (1) used.

In the esterification step (i), the compound of the general formula (1) is reacted at a molar ratio of 4-30 times, preferably 5-25 times, more preferably 8-20 times to the carboxylic acid halide of the general formula (2). When the molar ratio of the compound of the general formula (1) is lower than the above range, an oligoester is a main product. When the molar ratio of the compound of the general formula (1) is higher than the above range, there is no difference in the reaction selectivity but also the volume efficiency is deteriorated.

In the production method of the invention, a solvent may be used for the purpose of dissolving the starting materials and the product. As the solvent may be used the aforementioned organic base as it is, or the other organic solvent not obstructing the reaction may be used. As such a solvent are mentioned, for example, ether series solvents such as dimethyl ether, dioxane and the like.

In the esterification step (i), the way of charging the starting materials is not particularly limited, but there is usually adopted a way of adding the carboxylic acid halide of the general formula (2) dropwise to the solution of the compound of the general formula (1). The dropwise addition rate of the carboxylic acid halide is not particularly limited and may be properly determined within a range capable of holding the desirable temperature in the esterification step (i). The addition time is generally about 2-20 hours. After the addition of the carboxylic acid halide is completed, a maturing time may be properly introduced, and there is usually adopted a maturing time of about 1-10 hours.

The esterification step (i) is carried out commonly at −20° C. to 80° C., preferably at −10° C. to 60° C., more preferably at 0° C. to 50° C. When the temperature is too low, the reaction rate lowers and a longer time is required. On the other hand, when the temperature is too high, there is a tendency that the reaction selectivity lowers at the termination time of the oligomer decomposition step (ii).

The oligomer decomposition step (ii) is carried out usually at 105° C. to 140° C., preferably at 110° C. to 140° C., more preferably at 110° C. to 130° C., most preferably 115° C. to 130° C., particularly at 115° C. to 125° C. When the temperature is too low, the reaction rate lowers and a longer time is required. On the other hand, when the temperature is too high, there is a tendency that skeleton balance collapses depending on the kind of the diester body and also a by-product may be observed by heat history.

The time required for the oligomer decomposition step (ii) differs in accordance with the molar ratio of the compound of the general formula (1) to the carboxylic acid halide of the general formula (2), but is commonly about 2-20 hours. When the time is too short, the decomposition of the oligomer is insufficient and the ratio of diester body/oligoester body tends to be deteriorated. On the other hand, when maturing is conducted for a longer time, it is feared to produce a by-product and a decomposed product by heat history.

In the production method of the invention, when the base or the organic solvent is used, the desired temperature may not be attained at the decomposition of the oligomer depending on the kind of the base or solvent. In this case, the temperature may be raised to the desirable oligomer decomposition temperature during or after the distilling off of the base or solvent used. When the desired temperature is attained during the distilling off of the basic compound, the oligomer decomposition reaction occurs. However, the efficiency of the oligomer decomposition is high as the concentration of the compound of the general formula (1) becomes higher, so that it is preferable to conduct the oligomer decomposition after the basic compound is distilled off.

The compound of the general formula (3) obtained by the production method of the invention can be isolated from the reaction mixture by any well-known method. There are mentioned a method wherein the basic compound and the compound of the general formula (1) used in the reaction as well as the organic solvent when it is used in the reaction are distilled off and dried by the operation such as distillation under a reduced pressure or the like, a method wherein a poor solvent for the compound of the general formula (3) is added to the reaction mixture for reprecipitation, a method wherein a reaction mixed solution is added with water and an organic solvent immiscible with water to extract into an organic layer, and so on. In some cases, the purification may be conducted by recrystallization. As the poor solvent for the compound of the general formula (3) is usually used water. As the organic solvent immiscible with water are used esters such as ethyl acetate, butyl acetate and the like; and ketones such as methylisobutyl ketone, diisobutyl ketone and the like.

In the production method of the invention, when resorcin is used as the compound of the general formula (1), the compound represented by the general formula (4) is obtained, but an oligoester body represented by the general formula (5) may be included in the product. Typically, the product includes 60-100% by weight of the compound of the general formula (4), and 0-20% by weight of a compound represented by n=2 in the general formula (5), 0-10% by weight of a compound represented by n=3 in the general formula (5) and 10% by weight in total of compounds represented by n=4-6 in the general formula (5), preferably 0-30% by weight of compounds represented by the general formula (5). These ratios may be controlled by changing the molar ratio of the carboxylic acid halide of the general formula (2) to resorcin. That is, as the molar ratio of resorcin to the carboxylic acid halide becomes higher, the ratio of the oligoester body represented by the general formula (5) lowers. Even if these oligoester bodies are included in the product, they may be isolated from the reaction mixture in the same manner as the above isolation method for the compound of the general formula (3).

A preferable embodiment of the production method of the invention will be described below. Resorcin corresponding to 10 times mol of the carboxylic acid dihalide to be used is dissolved in an organic base of the same weight as in resorcin and held at 15° C. The carboxylic acid dihalide is added dropwise while maintaining this temperature to conduct esterification. At this stage, the reaction yield of the target compound represented by the general formula (4) is about 30-40%, and the oligoester body represented by the general formula (5) occupies the greater portion of the product. Thereafter, the basis compound is removed. In this course, an inner temperature gradually rises and may rise up to a decomposition temperature of an oligomer. Thereafter, the oligomer decomposition is carried out at 115-130° C. for 2 hours. At this step, the oligoester body of the general formula (5) is reacted with an excessive amount of resorcin (ester exchange reaction) in such a way that the composition of target diester body represented by the general formula (4) becomes rich. Then, the oligomer decomposed mass is discharged into water to conduct reprecipitation. Since the hydrolysis of the product is apprehended, there is frequently conducted a method wherein the oligomer decomposed mass is added dropwise into water usually cooled to about 5° C. to 30° C. The resulting precipitates are filtered, washed and dried at about 40-80° C. under a reduced pressure or under a stream of an inert gas.

In the above production method, it is commonly required to react an extremely excessive amount of the compound of the general formula (1) to the carboxylic acid halide of the general formula (2) in the presence of the basic compound, so that it is preferable in operation to efficiently recover unreacted compound of the general formula (1) to optimize a process. On the other hand, the compound represented by the general formula (3) can be produced simply and efficiently by (a) dissolving or suspending the compound of the general formula (1) in an organic solvent substantially immiscible with water and partially neutralizing with a basic compound; (b) adding and reacting a carboxylic acid halide represented by the general formula (2) dropwise to form an ester; (c) conducting a heat treatment at a temperature higher than that of the step (b) to decompose an oligomer in the ester: (d) contacting the mixture obtained in the step (c) with water to precipitate a product and subjecting to a solid-liquid separation operation and a drying to obtain a solid of the product; (e) adding an organic solvent substantially immiscible with water to a discharged water produced by the solid-liquid separation operation of the step (d) to extract an unreacted compound of the general formula (1) used as a starting material; and (f) adjusting a concentration in a solution of the compound of the general formula (1) in the organic solvent substantially immiscible with water obtained at the step (e) so as to render into a starting material in the step (a).

The organic solvent substantially immiscible with water means an organic solvent having a solubility in water of not more than 5% by weight, and is generally selected from organic solvents of ketone series, ether series and ester series. As the ketone series organic solvent are mentioned methylisobutyl ketone, ethylisobutyl ketone, diisobutyl ketone and so on. As the ether series organic solvent are mentioned diethyl ether, diisopropyl ether, dibutyl ether, cyclopentylmethyl ether and so on. As the ester series organic solvent are mentioned ethyl acetate, butyl acetate, amyl acetate and so on. Among them, methylisobutyl ketone is most preferable from viewpoints of reaction selectivity, recovering rate of the compound of the general formula (1), boiling point and the like.

As the basic compound used in the step (a) may be used organic base and inorganic base likewise the aforementioned step (i). Considering the cost, however, the inorganic base is preferable at the step (a), and particularly sodium hydroxide and potassium hydroxide are preferable. Such an inorganic base may be used as a solid or as an aqueous solution.

The amount of the basic compound used for the partial neutralization in the step (a) is usually 1.0-1.5 equivalent, preferably 1.0-1.2 equivalent, more preferably 1.0-1.05 equivalent of the carboxylic acid halide of the general formula (2) used in the reaction. When the amount is less than the above range, it is lacking than the stoichiometric amount. On the other hand, when it exceeds the above range, the yield tends to be lowered.

The esterification step (b) is carried out while charging the carboxylic acid halide of the general formula (2) dropwise. At this moment, the molar ratio of the compound of the general formula (1) to the carboxylic acid halide of the general formula (2), dropwise addition rate and time of the carboxylic acid halide, maturing time and the lie are the same as in the above step (i).

The esterification step (b) is carried out usually at $-20°$ C. to $50°$ C., preferably at $-10°$ C. to $40°$ C., more preferably $0°$ C. to $30°$ C. When the temperature is lower than the above range, the reaction rate lowers and a long time is taken. On the other hand, when the temperature is higher than the above range, the reaction selectivity at the time of ending the oligomer decomposition step tends to be lowered depending upon the kind of the carboxylic acid halide used.

The concentration in the esterification step (b) is not particularly limited as long as there can be ensured liquid sufficiently conducting agitation within the desired temperature range and is usually 5-60 weight %, preferably 10-55 weight %, more preferably 20-50 weight % as a charge concentration of the compound of the general formula (1) in the step (a). When the concentration is lower than the above range, the volume efficiency is low. While, when the concentration is higher than the above range, the viscosity becomes higher and there is a tendency of causing troubles in the agitation.

When an inorganic base is used as a basic substance in the step (a), a neutralized water is produced. Further, when using an aqueous solution of an alkaline metal hydroxide or the like, water derived from the basic compound is existent in the reaction system. As the procedure proceeds onto the oligomer decomposition step (c) at a state of including water in the system, the hydrolysis of the product is apprehended, so that it is required to remove water after the esterification step (b). In many cases, water has an azeotropic composition with the used organic solvent substantially immiscible with water, so that water is distilled off by a well-known azeotropic dehydration operation while returning the organic solvent separated from the distillate to the system. Typically, the water concentration in the system is not more than 2 weight %, preferably not more than 1 weight % as a measure of dehydration.

The temperature of the oligomer decomposition step (c) is required to be higher than the temperature in the step (b) likewise the aforementioned step (ii). In the oligomer decomposition step (c), the esterified reaction mixture (possibly a dehydrated mixture) may be used as it is, or the mixture after the removal of the organic solvent may be used. Since there is a case that the temperature does not reach to the desired oligomer decomposition temperature depending upon the organic solvent used, the temperature is often raised to the oligomer decomposition temperature during or after the distilling out of the organic solvent. When the organic solvent is distilled out, there is a merit that water not removed sufficiently in the azeotropic dehydration due to the interrelation of solubility can be removed. The distillation may be conducted while gradually raising the inner temperature under a constant reduced pressure or by adjusting the reduced pressure so as to render the inner temperature into a constant level.

The oligomer decomposition step (c) is dependent on the kind of the compound or temperature, but is usually carried out for about 2-20 hours. Moreover, a time when the temperature is raised while distilling out the organic solvent is included. When the time is shorter than the above range, the decomposition of the oligomer is insufficient and the composition of the product is rich in the oligomer. On the other hand, when the time is longer than the above range, the change of the composition is not observed and the heat treatment comes to nothing, and the formation of by-product may be observed by heat history in some cases.

When the oligomer decomposition step (c) is conducted without removing the organic solvent, the subsequent step (d) is willing to be directly conducted, or the step (d) may be conducted after the removal of the organic solvent. When the ratio of the amount of the organic solvent used to water as a poor solvent is high, it may be badly influenced on the precipitation separation, so that the step (d) is frequently conducted after the amount of the solvent is reduced by concentration or the like. As a measure of concentration, the content of the organic solvent in the mixed solution after the concentration is not more than 20 weight %, preferably not more than 10 weight %.

The step (d) is a step wherein the mixed solution after the end of the reaction at the oligomer decomposition step (c) is contacted with water to precipitate a product. The solvent used in the step (d) is basically a poor solvent to the compound of the general formula (3) as a product but may be a good solvent to the compound of the general formula (1) as a starting material. Typically, water is used.

Water used as a poor solvent in the step (d) is used in an amount of 5-100 times by weight to the reaction mixture. When the amount is lower than the above range, the precipitation is insufficient and the yield is low. While, when it exceeds the above range, the volume efficiency is deteriorated.

When the reaction mixture is contacted with water as a poor solvent at the step (d), the temperature is commonly $0°$ C. to $40°$ C., preferably $0°$ C. to $25°$ C. When the temperature is higher than this range, the hydrolysis of the product is apprehended.

The method of contacting the reaction mixture with water as a poor solvent in the step (d) is not particularly limited as long as the desired temperature may be maintained. Since the reaction mixture is at a state of distilling out a most of the solvent and dissolving the product into the compound of the general formula (1) as a starting material, the fluidity can not be frequently maintained below the oligomer decomposition temperature depending on the kind of the compound. Therefore, there is adopted a method wherein precipitates are separated while charging dropwise or separately the warmed reaction mixture into water set to the desired temperature. The charging rate is not particularly limited as long as the desired temperature can be maintained, but the step (d) is carried out over 0.5 hour to 10 hours. When the time is shorter than this range, the filtering rate of the resulting crystal tends to become slow. On the other hand, when the time is longer than the above range, the state is particularly unchangeable, but the change of crystal size is caused due to shearing or breaking action through agitation, and hence the filtering rate may become slow.

In the step (d), precipitates obtained by contacting with water are separated by solid-liquid separation operation such as filtration, centrifugal separation or the like.

Also, the wetted body separated by the solid-liquid separation operation in the step (d) is dried under an atmospheric pressure or a reduced pressure. The drying temperature is not particularly limited, but is 20° C. to 120° C., preferably 40° C. to 80° C. When the temperature is higher than this range, the hydrolysis of the product is apprehended. Moreover, the drying time may be shortened while suppressing the hydrolysis by drying while continuously or stepwise raising the temperature from an initial stage to last stage of the drying.

The dried solid obtained in the step (d) may be subjected to a purification through recrystallization or a column purification.

In water discharged by the solid-liquid separation operation in the step (d) is included the compound of the general formula (1) excessively used as a starting material. In this connection, the step (e) is a step wherein the same organic solvent as used in the reaction and substantially immiscible with water is added to the discharge water to extract the compound of the general formula (1).

The amount of the organic solvent used for the extraction in the step (e) is not particularly limited but is properly determined by target recovering ratio, extraction number and the like. In general, the organic solvent is used in an amount of 0.05-10 times, preferably 0.1-5 times, further preferably 0.2-2 times by weight to the discharge water per one extraction operation. When the amount is lower than this range, the extraction is insufficient, while when it is higher than the above range, the improvement of the extraction ratio is not observed, which brings about the deterioration of the volume efficiency.

The extraction number in the step (e) is not particularly limited and is properly determined by the target recovering ratio, but conditions (solvent amount, time, temperature) so as to render the number into about 1-3 may be frequently determined. Also, the extraction time is not particularly limited. The extraction is generally conducted for about 0.5-2 hours and thereafter the extract is left to stand for about 0.5-2 hours, and then liquid separation may be conducted.

In the step (e), the extraction temperature is not particularly limited, but is commonly 5° C. to 80° C., preferably 10° C. to 70° C., more preferably 20-50° C. In the discharge water generated at the step (d) may be existent the compound of the general formula (3) of an amount corresponding to its solubility. In this case, the compound of the general formula (3) is extracted into the organic solvent by the extraction operation of the step (e) and subjected to concentration at the subsequent step (f) and then supplied as a staring material to be charged, which brings about the improvement of the yield in subsequent reaction. Therefore, when the extraction is carried out at a temperature higher than the above range, there is a possibility that the improvement of yield in the subsequent reaction is not brought about by the hydrolysis of the compound of the general formula (3).

In the step (e), it is preferable to adjust pH of water layer in the extraction of the unreacted compound of the general formula (1) used as a starting material to 6.5-7.5. When pH in the extraction is not less than 6.5, the possibility of lowering the reaction yield due to the incorporation of an acid component can be reduced. Also, when pH is not more than 7.5, the extraction loss to water layer is reduced and the stable extraction can be attained. In this case, pH can be properly adjusted according to the well-known method, for example, by adding an acid such as acetic acid, hydrochloric acid or sulfuric acid, or a base such as sodium hydroxide, potassium hydroxide or the like.

The step (f) is a step wherein the extract obtained in the step (e) is concentrated so as to use at the step (a) as a starting material. Typically, the compound of the general formula (1) is concentrated to the same concentration as in the charging and an amount of the compound of the general formula (1) corresponding to the amount consumed in the reaction is supplemented and thereafter the organic solvent is added to adjust the concentration. In the extract is included water corresponding to a saturated solubility, which may be distilled out together with the solvent. Alternately, the azeotropic dehydration with the solvent is first conducted to render the system into a substantially non-aqueous system and thereafter the concentration operation may be conducted.

In the step (f), the temperature in the concentration or azeotropic dehydration is not particularly limited, but is usually 20° C. to 100° C., preferably 30° C. to 70° C., more preferably 40° C. to 60° C. under an atmospheric pressure or a reduced pressure. When the temperature is lower than the above range, a higher vacuum is required and burden of equipment such as vacuum pump, condenser or the like becomes large. When the temperature is higher than the above range, the hydrolysis of the compound of the general formula (3) included in the extract is apprehended.

A preferable embodiment of the production method of the invention including the steps (a)-(f) is shown below. Dihydroxybenzene corresponding to 10 mol times of a carboxylic acid halide as a starting material is dissolved in the same amount by weight of a water immiscible solvent and partially neutralized by adding an aqueous solution of 25 wt %-30 wt % of NaOH having 1.0-1.1 equivalent to a functional group of the carboxylic acid halide. Thereafter, it is cooled to 10° C. and the carboxylic acid halide is added continuously or separately while holding at 10° C. to 15° C. to conduct esterification reaction, and after the end of the addition, maturing is carried out for about 1 hour. At this stage, the yield of the target dihydroxybenzene derivative represented by the general formula (3) is about 30%-40%, and an oligomer comprises a major portion. Thereafter, azeotropic dehydration with the water immiscible solvent is conducted at 40° C. to 65° C. to reduce the water concentration in the reaction system to not more than 1 weight %, and then the water immiscible solvent is distilled out of the system. As the distillation proceeds, the inner temperature rises, but the removal of the solvent is stopped at a time of raising to an oligomer decomposition temperature. Then, the oligomer decomposition is conducted at 120° C. for 2 hours. At this stage, the composition of the product is determined and the target dihydroxybenzene derivative represented by the general formula (3) is a main product. Thereafter, the oligomer-decomposed mass is warmed to an extent capable of holding the fluidity and discharged continuously or separately into water cooled to 5° C. to 25° C. to conduct reprecipitation. The resulting precipitates are filtered and washed with water to remove dihydroxybenzene attached thereto, and then dried at about 40-80° C. under a reduced pressure or in an inert gas stream.

EXAMPLES

The invention will be described in detail with reference to examples and comparative examples, but the invention is not limited to the following examples. In the examples, analytical conditions of HPLC are as follows.

1. Analysis of bis(3-hydroxyphenyl) adipate, bis(3-hydroxyphenyl) sebacate and resorcin
   column: A-312 ODS made by YMC
   column temperature: 40° C.
   eluting solution: methanol/water=7/3 (adjusted pH=3 with phosphoric acid)
   detection: UV (254 nm)
2. Analysis of oligomer
   column: A-312 ODS made by YMC
   column temperature: 40° C.
   eluting solution: acetonitrile/water=8/2 (adjusted to pH=3.5 with acetic acid)
   detection: UV (254 nm)

Example A-1

A solution of 330.6 g (3.0 mol) of resorcin in 600.0 g of pyridine is gradually added with 54.9 g (0.30 mol) of adipoyl chloride while holding on an ice bath below 15° C. After the end of the addition, the resulting reaction mixture is raised to room temperature, and then pyridine is distilled out from the reaction mixture under a reduced pressure. Finally, the inner temperature is about 72° C. Thereafter, the reaction mixture is raised to 120° C. and matured at the same temperature for 2 hours. The resulting reaction mixture is discharged into 1200 g of water held at 15° C. and cooled to 3-5° C. with ice to separate out precipitates. The separated precipitates are filtered and washed with water, and the resulting wetted body is dried under a reduced pressure to obtain 89.8 g of white-light yellowish powder (yield (crude) 90.6%/adipoyl chloride). As an analytical result of the resulting powder through HPLC, bis(3-hydroxyphenyl) adipate in the powder is 89.3 weight %. In the powder are also included 7.3 weight % of a compound represented by the general formula (5) with n=2 (hereinafter referred to oligomer-1), 2.0 weight % of a compound represented by the general formula (5) with n=3 (hereinafter referred to oligomer-2), and 2.5 weight % of starting resorcin.

Example A-2

A solution of 330.6 g (3.0 mol) of resorcin in 600.0 g of pyridine is gradually added with 54.9 g (0.30 mol) of adipoyl chloride while holding on an ice bath below 15° C. After the end of the addition, the resulting reaction mixture is gradually raised and matured at 116° C. for 2 hours. Thereafter, pyridine is distilled of under a reduced pressure while holding at 80° C. The resulting reaction mixture is discharged into 1200 g of water held at 15° C. and cooled with ice to separate out precipitates. The separated precipitates are filtered and washed with water, and the resulting wetted body is dried under a reduced pressure to obtain 89.8 g of white-light yellowish powder (yield (crude) 89.7%/adipoyl chloride). As an analytical result of the resulting powder through HPLC, bis(3-hydroxyphenyl) adipate in the powder is 88.9 weight %. In the powder are also included 7.2 weight % of oligomer-1, 2.2 weight % of oligomer-2, and 2.2 weight % of starting resorcin.

Example A-3

A solution of 330.6 g (3.0 mol) of resorcin in 600.0 g of pyridine is gradually added with 71.7 g (0.30 mol) of sebacic chloride while holding on an ice bath below 15° C. After the end of the addition, the resulting reaction mixture is raised to room temperature, and then pyridine is distilled out from the reaction mixture under a reduced pressure. Finally, the inner temperature is about 80° C. Thereafter, the reaction mixture is raised to 120° C. and matured at the same temperature for 2 hours. The resulting reaction mixture is discharged into 1200 g of water held at 15° C. and cooled to 3-5° C. with ice to separate out precipitates. The separated precipitates are filtered and washed with water, and the resulting wetted body is dried under a reduced pressure to obtain 105.3 g of white-light yellowish powder (yield (crude) 90.8%/sebacic chloride). As an analytical result of the resulting powder through HPLC, bis(3-hydroxyphenyl) sebacate in the powder is 99.1 weight %. In the powder is also included 0.25 weight % of starting resorcin.

Comparative Example A-1

A solution of 330.6 g (3.0 mol) of resorcin in 600.0 g of pyridine is gradually added with 54.9 g (0.30 mol) of adipoyl chloride while holding on an ice bath below 15° C. After the end of the addition, the resulting reaction mixture is raised to room temperature and left to stand around the clock to complete the reaction. Then, pyridine is distilled out from the reaction mixture under a reduced pressure and finally the inner temperature is about 80° C. The resulting reaction mixture is discharged into 1200 g of water held at 15° C. to separate out precipitates. The separated precipitates are filtered and washed with water, and the resulting wetted body is dried under a reduced pressure to obtain 75 g of white-light yellowish powder (yield (crude) 75.7%/adipoyl chloride). As an analytical result of the resulting powder through HPLC, bis(3-hydroxyphenyl) adipate in the powder is 72 weight %. In the powder are also included 10 weight % of oligomer-1, 5 weight % of oligomer-2, and 2.5 weight % of starting resorcin.

Comparative Example A-2

The reaction is carried out in the same charging and operation as in Comparative Example A-1 and left to stand around the clock to complete the reaction. Then, pyridine is distilled out from the reaction mixture under a reduced pressure and finally the inner temperature is about 70° C. The resulting reaction mixture is discharged into 1200 g of water held at 15° C. to separate out precipitates. The separated precipitates are filtered and washed with water, and the resulting wetted body is dried under a reduced pressure to obtain 68 g of white-light yellowish gooey solid (yield (crude) 68.6%/adipoyl chloride). As an analytical result of the resulting solid through HPLC, bis(3-hydroxyphenyl) adipate in the powder is 65 weight %. In the powder are also included 15 weight % of oligomer-1, 7 weight % of oligomer-2, 2 weight % of a compound represented by the general formula (5) with n=4 (hereinafter referred to oligomer-3), and 2.4 weight % of starting resorcin.

Comparative Example A-3

A solution of 330.6 g (3.0 mol) of resorcin in 600.0 g of pyridine is gradually added with 71.7 g (0.30 mol) of sebacic chloride while holding on an ice bath below 15° C. After the end of the addition, the resulting reaction mixture is raised to room temperature, and then pyridine is distilled out from the reaction mixture under a reduced pressure. Finally, the inner temperature is about 80° C. The resulting reaction mixture is discharged into 1200 g of water held at 15° C. and cooled to 3-5° C. with ice to separate out precipitates. The separated precipitates are filtered and washed with water, and the resulting wetted body is dried under a reduced pressure to obtain 86.9 g of white-light yellowish powder (yield (crude) 75.0%/ sebacic chloride). As an analytical result of the resulting powder through HPLC, bis(3-hydroxyphenyl) sebacate in the powder is 79.1 weight %. In the powder are also included 15 area % of a component being considered to be a dimer, and 0.4 weight % of starting resorcin.

Comparative Example A-4

A solution of 330.6 g (3.0 mol) of resorcin in 600.0 g of pyridine is heated to 120° C. 54.9 g (0.30 mol) of adipoyl chloride is gradually added while holding at the same temperature. As an analytical result of the reaction liquid after the end of the addition, the reaction yield of bis(3-hydroxyphenyl) adipate is only 54%, and plural unclear peaks are observed.

In Comparative Examples A-1 and A-2, the ratio of diester body/oligoester body largely differs but also the difference in the yield appears due to the difference of the operation for the removal of pyridine as a separation step while conducting the same reaction.

In Examples A-1 and A-2, approximately constant yield and ratio of diester body/oligoester body are maintained by introducing an operation of maturing at 120° C. (oligomer decomposition) irrespectively of the difference in the removal of pyridine.

As seen from Comparative Example A-4, when the esterification reaction itself is carried out at a temperature of oligomer decomposition step, the selectivity considerably lowers due to the thermal decomposition of acid chloride or the like.

Example B-1

110.2 g (1.0 mol) of resorcin (hereinafter abbreviated as RS) is dissolved in 110 g of methylisobutyl ketone (hereinafter abbreviated as MIBK) and partially neutralized by adding 26.7 g (0.204 mol) of an aqueous solution of 30.6 weight % of NaOH. Thereafter, the resulting mixture is cooled to 10° C. and added dropwise with 18.3 g (0.10 mol) of adipoyl chloride (hereinafter abbreviated as ADC) over 1 hour while maintaining at 10-15° C. to conduct esterification reaction, which is matured at the same temperature for 1 hour. b Thereafter, azeotropic dehydration is carried out under a reduced pressure (around 40 torr) while raising the temperature. The azeotropic dehydration is stopped at a time that an inner temperature comes to 65° C. after about 3 hours. The water content in the system is 0.3 weight %. Then, MIBK is distilled out under a reduced pressure (30 torr) while raising the temperature. The removal of MIBK is ended at a tome that the inner temperature comes to 120° C. after about 2 hours. In this case, the concentration of MIBK in the system is 5 weight %. After the oligomer decomposition is conducted by maturing at the same temperature for 2 hours, the reaction mixture is discharged into 540 g of water cooled to 5° C. over 30 minutes to separate out crystal. The crystal is filtered by filtration with a Buchner flask under a reduced pressure, washed with 540 g of water and dried under a reduced pressure at 60° C. for 15 hours to obtain 29.8 g of white-light yellowish powder (yield (crude) 90.3%/ADC). As an analytical result through HPLC, bis(3-hydroxyphenyl) adipate is 89/0 weight %, and an oligomer (dimer) is 7.4 weight %, and the starting resorcin is 3.1 weight %. The results are shown in Table 1.

On the other hand, 609.9 g of a filtrate obtained by filtration and washing is subjected to extraction for 1 hour-liquid separation by standing for 1 hour at 30° C. with 492.8 g in total of MIBK obtained by adding new MIBK to 106 g of MIBK recovered after the oligomer decomposition two times. Resorcin in MIBK layer is 98.0% to RS in the filtrate. Subsequently, water and MIBK are distilled out at 60° C./20 torr to prepare 196.5 g of 44.0 weight % RS/MIBK solution.

Into the resulting RS/MIBK solution is supplied and dissolved 23.74 g of a deficiency RS to prepare 220.2 g of 50 weight % RS/MIBK solution.

Example B-2

Partial neutralization is conducted by adding 26.7 g (0.204 mol) of an aqueous solution of 30.6 weight % NaOH to 220.2 g (RS: 1.0 mol) of 50 weight % RS/MIBK solution obtained in Example B-1. Thereafter, the same procedure as in Example B-1 is carried out to obtain 30.4 g of pale brown powder (yield (crude) 93.8%/ADC). As an analytical result through HPLC, bis(3-hydroxyphenyl) adipate is 86.5 weight %, and an oligomer (dimer) is 8.2 weight %, and the starting resorcin is 3.0 weight %. The results are shown in Table 1.

On the other hand, 611.2 g of a filtrate obtained by filtration and washing is subjected to extraction for 1 hour-liquid separation by standing for 1 hour at 30° C. with 492.8 g in total of MIBK obtained by adding new MIBK to 108 g of MIBK recovered after the oligomer decomposition two times. Resorcin in MIBK layer is 98.1% to RS in the filtrate. Subsequently, water and MIBK are distilled out at 60° C./20 torr to prepare 196.3 g of 44.0 weight % RS/MIBK solution.

Into the resulting RS/MIBK solution is supplied and dissolved 23.9 g of a deficiency RS to prepare 220.2 g of 50 weight % RS/MIBK solution.

Example B-3

The same procedure as in Example B-2 is conducted using 220.2 g (RS: 1.0 mol) of 50 weight % RS/MIBK solution obtained in Example B-2. The composition ratio and yield (crude) of the resulting crystal are shown in Table 1.

Example B-4

The same procedure as in Example B-2 is conducted using 50 weight % RS/MIBK solution obtained in Example B-3. The composition ratio and yield (crude) of the resulting crystal are shown in Table 1.

Example B-5

The same procedure as in Example B-2 is conducted using 50 weight % RS/MIBK solution obtained in Example B-4. The composition ratio and yield (crude) of the resulting crystal are shown in Table 1.

Example B-6

The same procedure as in Example B-2 is conducted using 50 weight % RS/MIBK solution obtained in Example B-5. The composition ratio and yield (crude) of the resulting crystal are shown in Table 1.

Example B-7

The same procedure as in Example B-1 is repeated to obtain 29.7 g of white-light yellowish powder (yield (crude)

90.1%/ADC). As an analytical result through HPLC, bis(3-hydroxyphenyl) adipate is 88.9 weight %, and an oligomer (dimer) is 7.4 weight %, and the starting resorcin is 3.0 weight %. The results are shown in Table 2.

On the other hand, 610.5 g of a filtrate obtained by filtration and washing is adjusted to pH=7.0 (pH=6.3 before adjustment) with an aqueous solution of 30 weight % NaOH. The filtrate after the pH adjustment is subjected to extraction for 1 hour-liquid separation by standing for 1 hour at 30° C. with 492.8 g in total of MIBK obtained by adding new MIBK to 108 g of MIBK recovered after the oligomer decomposition two times. Resorcin in MIBK layer is 98.0% to RS in the filtrate. Subsequently, water and MIBK are distilled out at 60° C./20 ton to prepare 196.2 g of 44.0 weight % RS/MIBK solution.

Into the resulting RS/MIBK solution is supplied and dissolved 24.0 g of a deficiency RS to prepare 220.2 g of 50 weight % RS/MIBK solution.

Example B-8

Partial neutralization is conducted by adding 26.7 g (0.204 mol) of an aqueous solution of 30.6 weight % NaOH to 220.2 g (RS: 1.0 mol) of 50 weight % RS/MIBK solution obtained in Example B-7. Thereafter, the same procedure as in Example B-1 is carried out to obtain 30.3 g of pale brown powder (yield (crude) 93.6%/ADC). As an analytical result through HPLC, bis(3-hydroxyphenyl) adipate is 86.6 weight %, and an oligomer (dimer) is 8.2 weight %, and the starting resorcin is 3.1 weight %. The results are shown in Table 2.

On the other hand, the filtrate obtained by filtration and washing is treated in the same procedure as in Example B-7 to prepare 220.2 g of 50 weight % RS/MIBK solution.

Example B-9

The same procedure as in Example B-8 is conducted using 50 weight % RS/MIBK solution obtained in Example B-8. The composition ratio and yield (crude) of the resulting crystal are shown in Table 2.

Example B-10

The same procedure as in Example B-8 is conducted using 50 weight % RS/MIBK solution obtained in Example B-9. The composition ratio and yield (crude) of the resulting crystal are shown in Table 2.

Example B-11

The same procedure as in Example B-8 is conducted using 50 weight % RS/MIBK solution obtained in Example B-10, and subsequently a series of such operations are repeated 6 times. The composition ratio and yield (crude) of the resulting crystal are shown in Table 2.

TABLE 1

| Example | RS recycle (number) | Yield (crude) (%/ADC) | bis(3-hydroxyphenyl) adipate | dimer | RS |
|---|---|---|---|---|---|
| B-1 | 0 | 90.3 | 89.0 | 7.4 | 3.1 |
| B-2 | 1 | 93.8 | 86.5 | 8.2 | 3.0 |
| B-3 | 2 | 93.5 | 86.8 | 8.1 | 3.0 |
| B-4 | 3 | 93.8 | 86.4 | 8.4 | 3.3 |

TABLE 1-continued

| Example | RS recycle (number) | Yield (crude) (%/ADC) | bis(3-hydroxyphenyl) adipate | dimer | RS |
|---|---|---|---|---|---|
| B-5 | 4 | 93.4 | 85.9 | 8.9 | 2.9 |
| B-6 | 5 | 93.5 | 85.3 | 9.3 | 3.0 |

TABLE 2

| Example | RS recycle (number) | Yield (crude) (%/ADC) | bis(3-hydroxyphenyl) adipate | dimer | RS |
|---|---|---|---|---|---|
| B-7 | 0 | 90.1 | 88.9 | 7.4 | 3.0 |
| B-8 | 1 | 93.6 | 86.6 | 8.2 | 3.1 |
| B-9 | 2 | 93.5 | 86.9 | 8.0 | 2.9 |
| B-10 | 3 | 93.7 | 86.6 | 8.2 | 3.0 |
| B-11 | 10 | 93.6 | 86.5 | 8.3 | 2.9 |

As seen from the results of Tables 1 and 2, the product composition is substantially unchangeable even if resorcin is recycled.

As seen from the comparison between the results of Table 1 and the results of Table 2, the lowering of the reaction yield due to the incorporation of acid component is suppressed to make the fluctuation range of the product composition small by adjusting pH of the water layer in the extraction of resorcin to 6.5-7.5, and hence the lowering of the yield of bis(3-hydroxyphenyl) adipate as a target product can be suppressed more surely.

The invention claimed is:

1. A method of producing a compound represented by the following general formula (3):

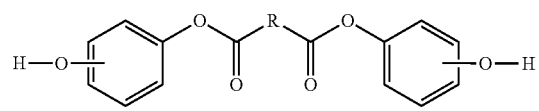

(3)

[wherein R is a bivalent aliphatic group having a carbon number of 1-16 or a bivalent aromatic group], which comprises a step (i) of reacting a compound represented by the following general formula (1):

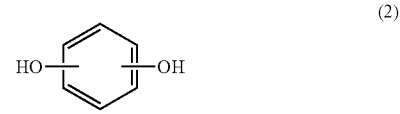

(2)

with a carboxylic acid halide represented by the following general formula (2):

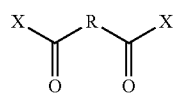
(2)

[wherein R is a bivalent aliphatic group having a carbon number of 1-16 or a bivalent aromatic group and X is a halogen atom] in the presence of a basic compound to form an ester, and a step (ii) of conducting a heat treatment after the step (i) to decompose an oligomer in the ester.

2. The method according to claim 1, wherein the compound of the general formula (1) is reacted at a molar ratio of 4-30 times with the carboxylic acid halide of the general formula (2).

3. The method according to claim 1, wherein the step (i) of forming the ester is carried out at −20° C. to 80° C.

4. The method according to claim 1, wherein the step (ii) of decomposing the oligomer is carried out at 110° C. to 140° C.

5. The method according to claim 1, wherein the basic compound is an organic base.

6. The method according to claim 1, wherein the compound of the general formula (3) is a compound represented by the following general formula (4):

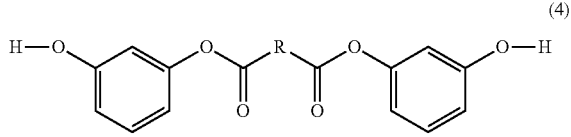
(4)

[wherein R is a bivalent aliphatic group having a carbon number of 1-16 or a bivalent aromatic group].

7. The method according to claim 1, which includes a step (a) of dissolving or suspending the compound of the general formula (1) in an organic solvent substantially immiscible with water and partially neutralizing with the basic compound;

a step (b) of adding the carboxylic acid halide of the general formula (2) dropwise and reacting to form an ester;

a step (c) of conducting a heat treatment at a temperature higher than that of the step (b) to decompose an oligomer in the ester;

a step (d) of contacting a mixture obtained in the step (c) with water to precipitate a product and subjecting to a solid-liquid separation operation and a drying to obtain a solid of the product;

a step (e) of adding an organic solvent substantially immiscible with water to a discharged water produced by the solid-liquid separation operation of the step (d) to extract an unreacted compound of the general formula (1) used as a starting material; and a step (f) of adjusting a concentration in a solution of the compound of the general formula (1) in the organic solvent substantially immiscible with water obtained at the step (e) so as to render into a starting material in the step (a).

8. The method according to claim 7, wherein the organic solvent substantially immiscible with water is selected from organic solvents of ketone series, ether series and ester series.

9. The method according to claim 7, wherein pH of water layer in the extraction of the unreacted compound of the general formula (1) used as a starting material is adjusted to 6.5-7.5.

10. The method according to claim 6, wherein the compound of the general formula (4) contains 0-30 weight % of a compound represented by the following general formula (5):

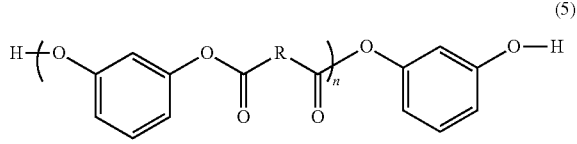
(5)

[wherein R is a bivalent aliphatic group having a carbon number of 1-16 or a bivalent aromatic group and n is an integer of 2-6].

* * * * *